(12) United States Patent
Durward et al.

(10) Patent No.: US 8,202,300 B2
(45) Date of Patent: Jun. 19, 2012

(54) SPINAL FLEXION AND EXTENSION MOTION DAMPER

(75) Inventors: Quentin John Durward, Dakota Dunes, SD (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 1064 days.

(21) Appl. No.: 11/953,185

(22) Filed: Dec. 10, 2007

(65) Prior Publication Data

US 2009/0149885 A1 Jun. 11, 2009

(51) Int. Cl.
*A61B 17/70* (2006.01)
(52) U.S. Cl. .......................... 606/248; 606/246; 606/250
(58) Field of Classification Search .......... 606/246–279; 623/17.11–17.16; 403/391, 396, 399
See application file for complete search history.

(56) References Cited

U.S. PATENT DOCUMENTS

| | | | |
|---|---|---|---|
| 2006/0229613 A1* | 10/2006 | Timm et al. | 606/61 |
| 2006/0241601 A1* | 10/2006 | Trautwein et al. | 606/61 |
| 2006/0293662 A1* | 12/2006 | Boyer et al. | 606/61 |
| 2007/0093832 A1 | 4/2007 | Abdelgany | |
| 2007/0118120 A1 | 5/2007 | Stevenson et al. | |
| 2007/0161993 A1* | 7/2007 | Lowery et al. | 606/61 |
| 2007/0173832 A1 | 7/2007 | Tebbe et al. | |

* cited by examiner

*Primary Examiner* — Eduardo C Robert
*Assistant Examiner* — Steven Cotroneo
(74) *Attorney, Agent, or Firm* — Rahman LLC

(57) ABSTRACT

An orthopedic damper system and method to control the degree of flexion and/or extension motion of the mobile vertebral segment while providing additional stability to the spine. The damper system includes an anchor having a spring hitch, a spring coupled to the spring hitch, and a cap coupled to the spring. The anchor is adapted to connect to a spinous process. The spring includes an inner hollow area adapted to accommodate the spring hitch. The cap includes an opening connected to an inner cavity that is adapted to accommodate the spring and the spring hitch.

20 Claims, 10 Drawing Sheets

SPINAL FLEXION AND EXTENSION MOTION DAMPER

BACKGROUND

1. Technical Field

The embodiments herein generally relate to medical devices, and, more particularly, to a spinal flexion and extension motion damper used during orthopedic surgeries.

2. Description of the Related Art

Patients who have a lumbar spinal fusion have an increased risk of having adjacent segment disease. Adjacent segment disease occurs after the spinal fusion in which the segment or the intervertebral disc and the facet joints are degenerated at the adjacent level above (and sometimes below) the lumbar fusion. This disease can produce severe pain that can affect the spinal cord's ability to properly function. Often, a disorder in one spinal component can lead to ultimate disorder, and finally pain in another component. These can also lead to spinal stenosis in which the spinal canal narrows and compresses the spinal cord and nerves. Laminectomy is a surgical procedure which is used for treating spinal stenosis by relieving pressure on the spinal cord. In this procedure, a part of the lamina (e.g., a part of the vertebra) is removed or trimmed to widen the spinal canal and create more space for the spinal nerves.

One way of accomplishing spinal fusion involves the use of devices such as a series of pedicle screw assemblies and connecting rods. Generally two pedicle screws are placed per vertebra and screwed into the pedicles. They include receiver elements for accommodating the connecting rods. Clamping elements are also adapted for receiving and joining the connecting rod to the screws. The spinal fusion using pedicle screw assemblies can be strengthened by attaching a spinal cross-connector between the connecting rods. Spinal cross-connectors are often used to provide additional stability to the devices. When the connecting rods are fastened in parallel on either side of the lamina, the pedicle screw assembly can be significantly strengthened by using a cross-connector to bridge the connecting rods. The cross-connectors are usually in the form of a rod having a clamp on each end for connecting with the connecting rods.

It is observed that more rigid spinal fixation systems may increase the risk of complications such as mechanical failure, adjacent segment disease, and device-related osteoporosis. To avoid these complications and concurrently obtain adequate immobilization, it is important to stabilize the affected mobile vertebral segment while controlling its degree of flexion and/or extension motion. Control of abnormal motions may relieve pain and prevent adjacent segment degeneration. Thus, an ideal spinal fixation system should provide dynamic stabilization as well as preservation of motion.

Traditional pedicle screw assemblies include a rubber bungee within a plastic tube placed between the heads of two pedicle screws. It provides dynamic stabilization to the motion segment, but typically requires extensive muscle dissection to place, and generally cannot work as an adjacent segment protector above a pedicle screw instrumented fusion. Another example is a solid device generally made up of titanium that is placed between two laminas to widen the inter-spinous and interlaminar space and to limit extension of the motion segment. In this way it is designed to relieve the symptoms of spinal stenosis but typically cannot work when a laminectomy has been performed. Furthermore, it generally has no ability to limit flexion, and is very rigid. Moreover, it typically cannot work to protect against adjacent segment disease. Also, these generally lack a limitation of the damping ability, which may lead to damage of the vertebrae during natural motion. Generally, there are no other known systems that stabilize the spine either rigidly or dynamically by utilizing the spinous process with a pedicle screw fixation assembly (regardless of the presence of an optional cross connector). Accordingly, there remains a need for a new damper system to control the degree of flexion and/or extension motion of the mobile vertebral segment while providing additional stability to the spine.

SUMMARY

In view of the foregoing, an embodiment herein provides an orthopedic damper system. The damper system includes a U-shaped anchor having a spring hitch, a spring coupled to the spring hitch, and a cap coupled to the spring. The spring includes an inner hollow area adapted to accommodate the spring hitch. The cap includes an opening connected to an inner cavity that is adapted to accommodate the spring and the spring hitch. The U-shaped anchor is adapted to connect to a spinous process.

The U-shaped anchor may include a plurality of arms each having a plurality of screw holes positioned opposite to the spring hitch and a slot configured between the plurality of arms. The damper system may include a plurality of retaining mechanisms adapted to fix into the spinous process. The plurality of screw holes may be adapted to accommodate the plurality of retaining mechanisms, and the slot may be adapted to accommodate the spinous process. The cap may include a hole and a cross-opening. Both the hole and the cross-opening may be positioned at an end of the cap opposite to the opening of the cap. The cross-opening of the cap may be adapted to accommodate a bar of a cross-connector assembly. The hole of the cap may be adapted to accommodate a fixation component to set the bar of the cross-connector assembly to the cap. The cross-connector assembly may be adapted to connect with a pair of polyaxial pedicle screw assemblies.

In another aspect, an apparatus for stabilizing a vertebral segment comprises an anchor, fixation means, a first spring coupled to the anchor, a cylindrical cap coupled to the first spring, and a second spring. The anchor is adapted to connect to a spinous process. The fixation means are adapted to attach the anchor to the spinous process. The anchor includes a clamping portion and a hitch connected to the clamping portion. The first spring includes an inner hollow area adapted to accommodate the hitch of the anchor. The cylindrical cap includes an opening leading to an inner cavity. The inner cavity is adapted to accommodate the first spring and the hitch of the anchor and a cross-opening having an opening.

The second spring may be positioned in the cylindrical cap and adjacent to the hitch. The cross-opening of the cylindrical cap may be adapted to accommodate a bar of a cross-connector assembly. The fixation means may include any of screws, fasteners, pins, nails, and corrugated teeth. The cylindrical cap may further include a hole adapted to accommodate a fixation component to set the bar of the cross-connector assembly to the cylindrical cap. The cross-connector assembly may be adapted to connect with a pair of oppositely positioned polyaxial pedicle screw assemblies.

Another aspect provides a method of controlling a degree of motion of a mobile vertebral segment, and includes fixing an anchor of a damper system to a spinous process, coupling a first spring to a portion of the anchor, inserting the first spring and the portion of the anchor into a cylindrical cap, inserting a bar of a cross-connector assembly through the cylindrical cap, connecting the cross-connector assembly to a pair of opposed polyaxial pedicle screw assemblies connected to oppositely positioned pedicles, biasing the first spring to control a motion of the spinous process and the oppositely positioned pedicles, inserting a second spring into the cylindrical cap and adjacent to the portion of the anchor in the cylindrical cap, and inserting a fixation component into the cylindrical cap to set the bar of the cross-connector assembly to the cylindrical cap.

The damper system includes the anchor, the first spring, and the cylindrical cap. The first spring includes an inner hollow area which is adapted to attach to the anchor. The cylindrical cap is adapted to accommodate the first spring and the portion of the anchor. The cross-connector assembly may be adapted to maintain and secure the posture of a vertebral column. The pair of opposed polyaxial pedicle screw assemblies may be adapted to connect two adjacent vertebrae by spinal fusion. The first spring may be adapted to control a degree of flexion of a vertebral segment. The anchor may include a slot configured to accommodate the spinous process.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1:
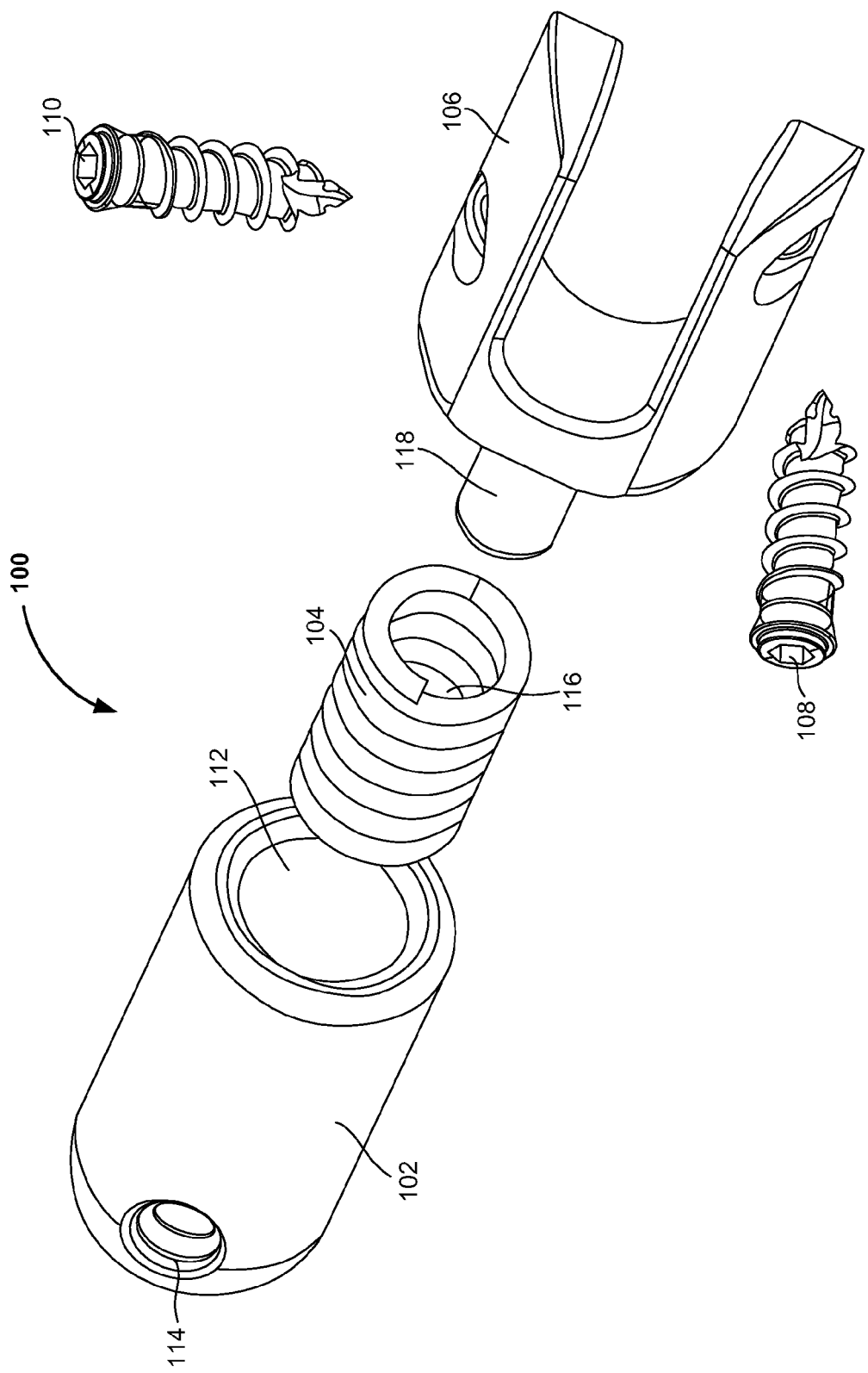
FIG. 1 illustrates an exploded perspective view of a damper system having a cylindrical cap, a first spring, an anchor, and two retaining mechanisms according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new damper system to control the degree of flexion and/or extension motion of the mobile vertebral segment while providing additional stability to the spine. The embodiments herein achieve this by providing an orthopedic damper system which includes an anchor having a hitch, a spring coupled to the spring hitch, and a cap coupled to the spring. The anchor is adapted to connect to a spinous process or a vertebral lamina. The spring includes an inner hollow area adapted to accommodate the spring hitch. The cap includes an opening connected to an inner cavity that is adapted to accommodate the spring and the spring hitch. Referring now to the drawings, and more particularly to FIGS. 1 through 7, where similar reference characters denote corresponding features consistently throughout the figures, there are shown preferred embodiments.

FIG. 1 illustrates an exploded perspective view of a damper system 100 having a cylindrical cap 102, a first spring 104, a U-shaped anchor 106, and two retaining mechanisms 108, 110 according to an embodiment herein. The retaining mechanisms 108, 110 may be embodied as two screws. The cylindrical cap 102 further includes an inner cavity 112 having an exposed opening and a hole 114 positioned at its rear. The hole 114 is positioned transverse to the longitudinal axis of the inner cavity 112 and opposite to the exposed opening of the cylindrical cap 102. The first spring 104 may be configured in other suitable configurations. The cylindrical cap 102 may accommodate the first spring 104 through the inner cavity 112. The first spring 104 further includes an inner hollow area 116. The U-shaped anchor 106 further includes a spring hitch 118 positioned at one side. The U-shaped anchor 106 along with the spring hitch 118 may fit into the inner hollow area 116 of the first spring 104. The two screws 108, 110 may be configured to fix into the U-shaped anchor 106.

Figure 2A:
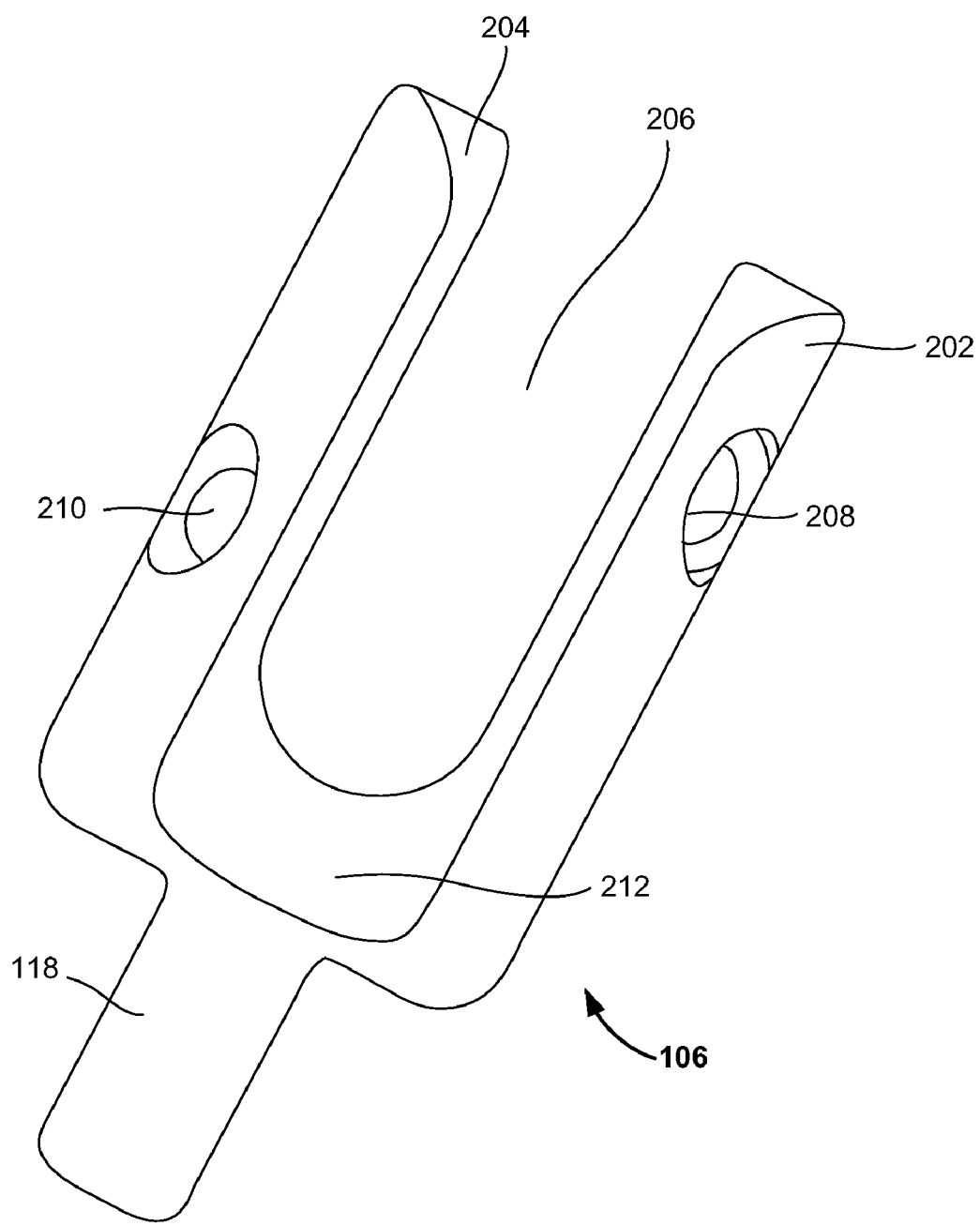
FIGS. 2A and 2B illustrate a front view and a perspective view, respectively, of the U-shaped anchor of FIG. 1 according to an embodiment herein.
Figure 2B:
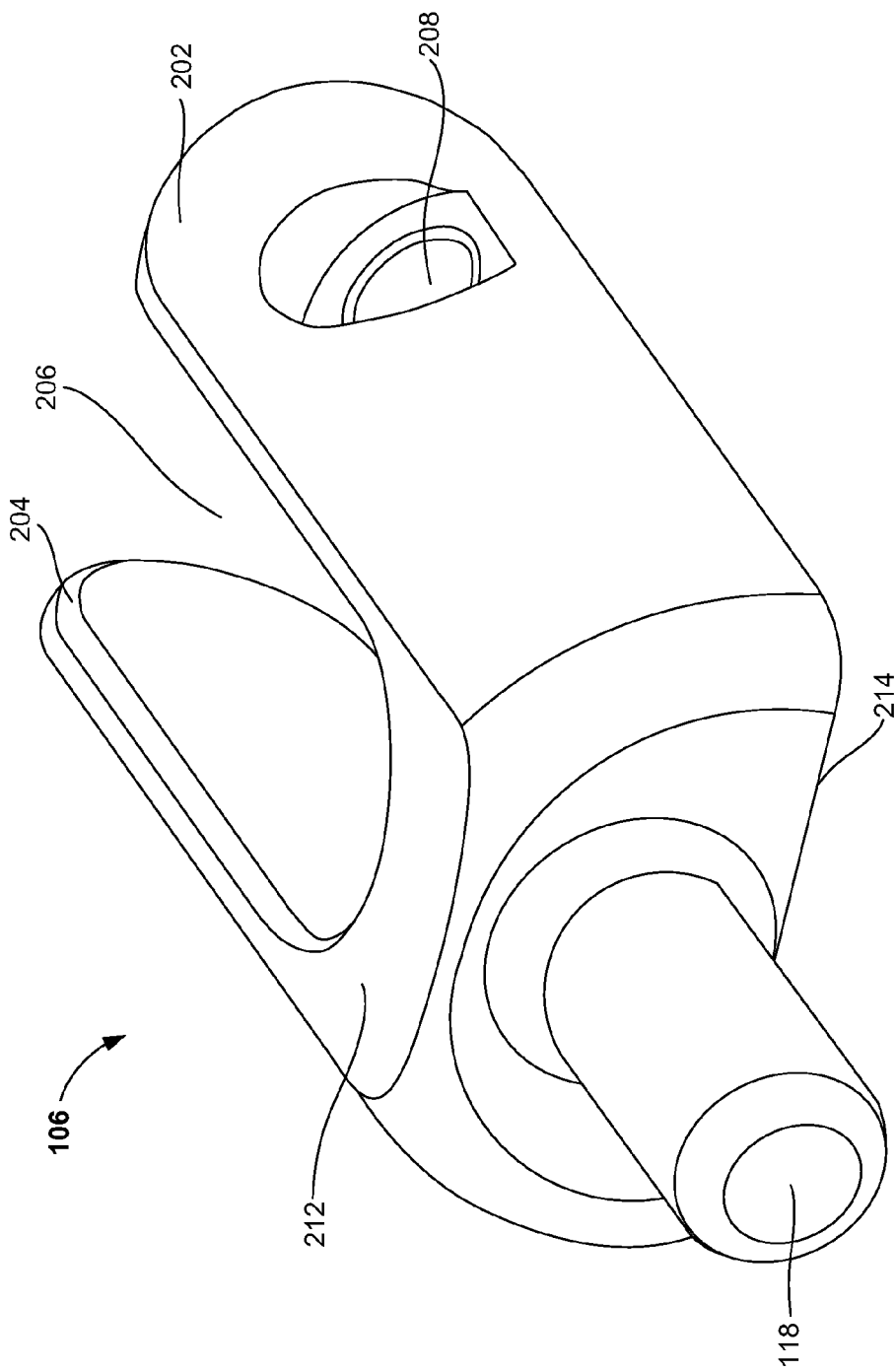

FIGS. 2A and 2B illustrate a front view and a perspective view, respectively, of the U-shaped anchor 106 of FIG. 1 according to an embodiment herein. The U-shaped anchor 106 includes a clamping portion which may be embodied as a pair of parallel and curved arms 202, 204. The arms are positioned on an opposite side of the spring hitch 118 and are connected to the spring hitch 118. A slot 206 is configured between the two arms 202, 204. The arm 202 has a screw hole 208 and the arm 204 has a screw hole 210. The screw holes 208, 210 are preferably not parallel or otherwise aligned to each other. The screw holes 208, 210 may be configured to accommodate the two screws 108, 110, respectively, to be fit into the arms 202, 204. Moreover, the two arms 202, 204 along with the slot 206 may accommodate a vertebral part (e.g., a lamina). Preferably, the U-shaped anchor 106 comprises flat top and bottom surfaces 212, 214, respectively.

Figure 3:
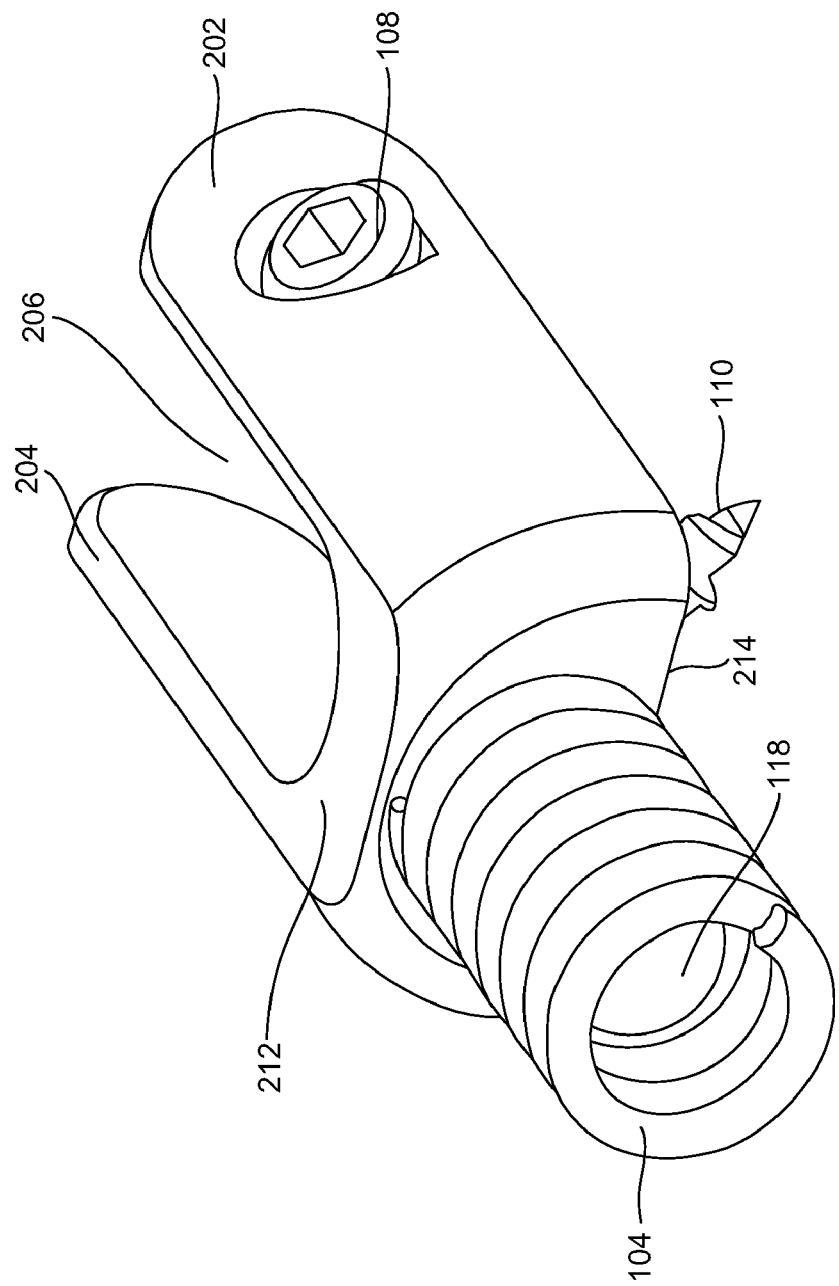
FIG. 3 illustrates an assembled view of the first spring, the anchor, and the two retaining mechanisms of FIG. 1 according to an embodiment herein.

FIG. 3 illustrates an assembled view of the first spring 104, the U-shaped anchor 106, and the two retaining mechanisms 108, 110 (e.g., the two screws 108, 110) of FIG. 1 according to an embodiment herein. The U-shaped anchor 106 along with the spring hitch 118 is fit into the inner hollow area 116 of the first spring 104. The screw 108 is fixed into the screw hole 208 of the first arm 202 and similarly the screw 110 is fixed into the screw hole 210 (not shown in FIG. 3) of the second arm 204.

Figure 4:
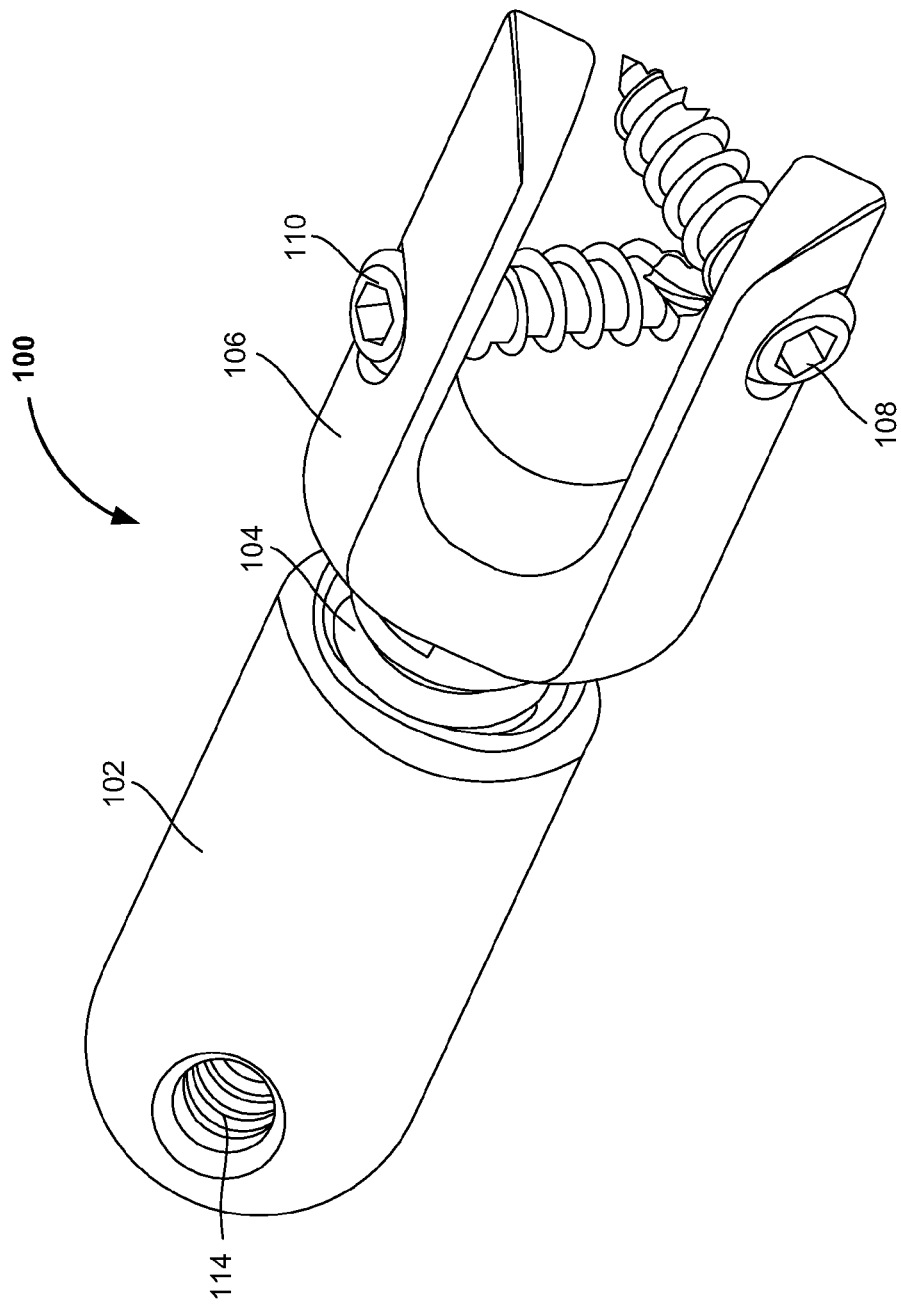
FIG. 4 illustrates an assembled view of the damper system of FIG. 1 according to an embodiment herein.

FIG. 4 illustrates an assembled view of the damper system 100 of FIG. 1 according to an embodiment herein. The cylindrical cap 102 accommodates the first spring 104 together with the U-shaped anchor 106. The spring hitch 118 of the U-shaped anchor 106 is fit into the inner hollow area 116 of the first spring 104. The two screws 108, 110 are fixed into the screw holes 208, 210, respectively, in such a way that they remain crossed to each other. This is accomplished by providing an angle to the configuration of the screw holes 208, 210 or to the screws 108, 110 themselves.

Figure 5A:
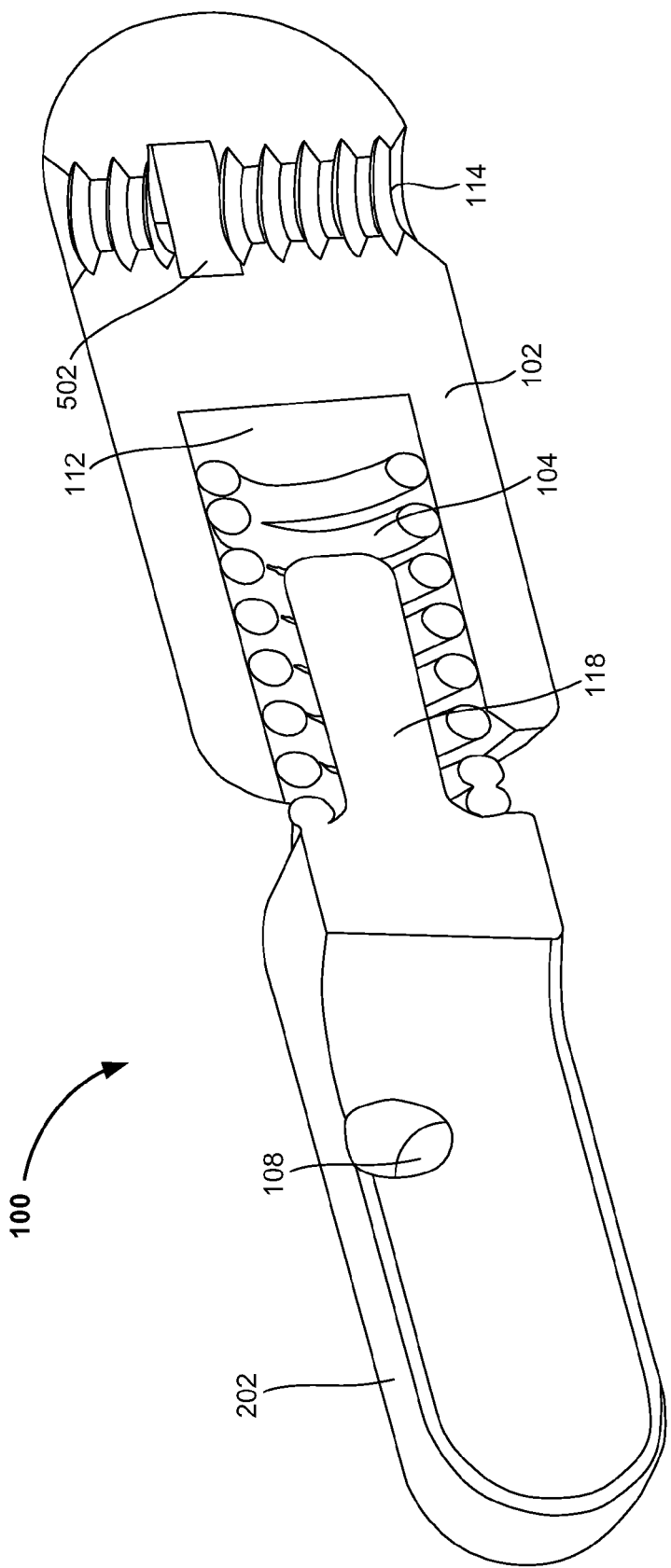
FIG. 5A illustrates a sectional view of the damper system of FIG. 4 according to a first embodiment herein.

FIG. 5A illustrates a sectional view of the damper system 100 of FIG. 4 according to a first embodiment herein. The cylindrical cap 102 further includes a cross-opening 502 which is positioned at an end of the cylindrical cap 102 opposite to the exposed opening of the cylindrical cap 102. The cross-opening 502 cuts the hole 114 horizontally. The hole 114 extends through the thickness of the cylindrical cap 102 and may be threaded at its inner side. Preferably, the spring hitch 118 does not cover the full length of the inner hollow area 116 of the first spring 104. Similarly the first spring 104 preferably does not cover the full length of the inner cavity 112 of the cylindrical cap 102. The first spring 104 may cover the full length of the inner cavity 112 when it becomes compressed.

Figure 5B:
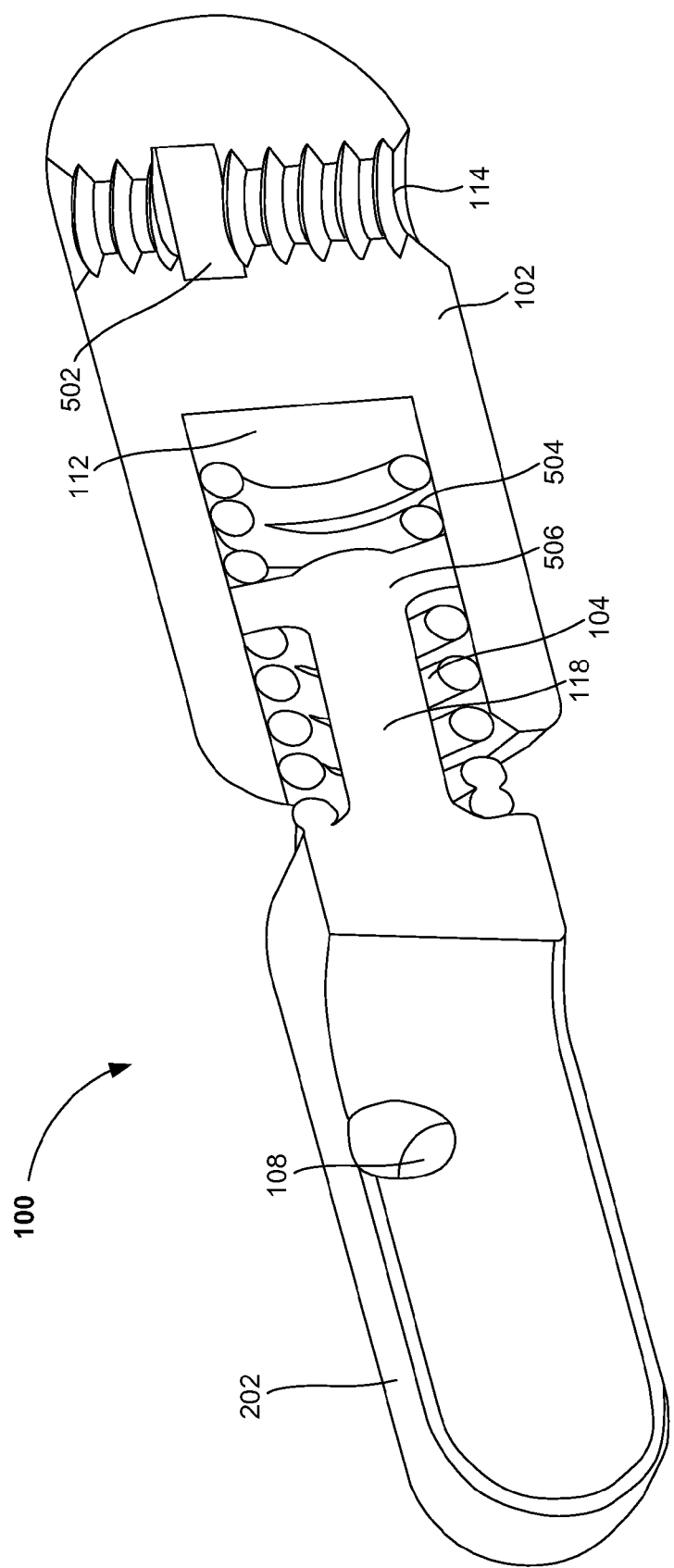
FIG. 5B illustrates a sectional view of the damper system of FIG. 4 according to a second embodiment herein.

FIG. 5B illustrates a sectional view of the damper system 100 of FIG. 4 according to a second embodiment. In this view, a second spring 504 is configured in the inner cavity 112 of the cylindrical cap 102 behind the spring hitch 118. Additionally, the spring hitch 118 in this embodiment comprises a flared end with an annual collar 506 at the tip of the spring hitch 118. The collar 506 provides for a biasing surface for both springs 104, 504.

The damper system 100 acts as a shock absorber (e.g., any mechanical device designed to smooth out or damp a sudden shock impulse). During the movement of the vertebrae when the vertebral segment receives some sudden forces, the first spring 104 may control a degree of flexion of a vertebral segment and damper the dynamic flexion and extension forces.

Figure 6A:
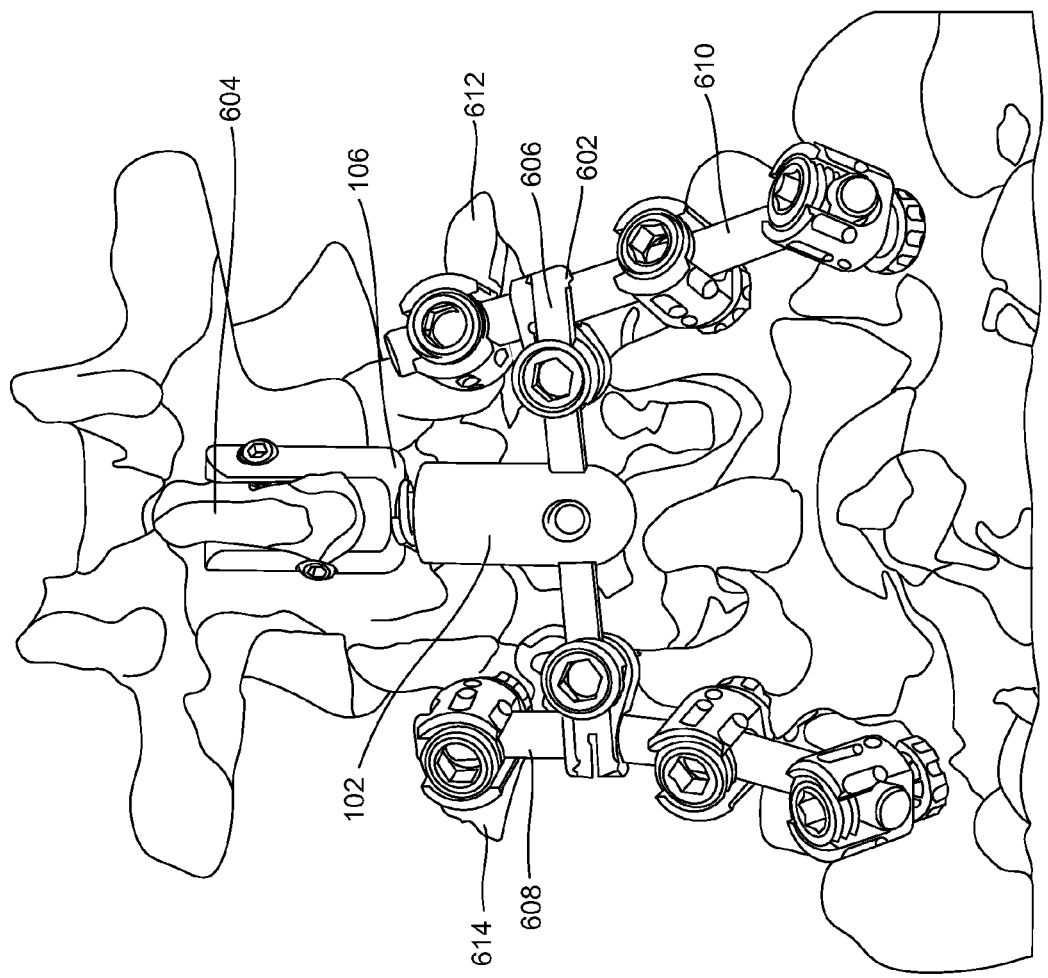
FIGS. 6A and 6B illustrate a front view and a side view, respectively, of the damper system of FIG. 4 assembled into a vertebra according to an embodiment herein.
Figure 6B:
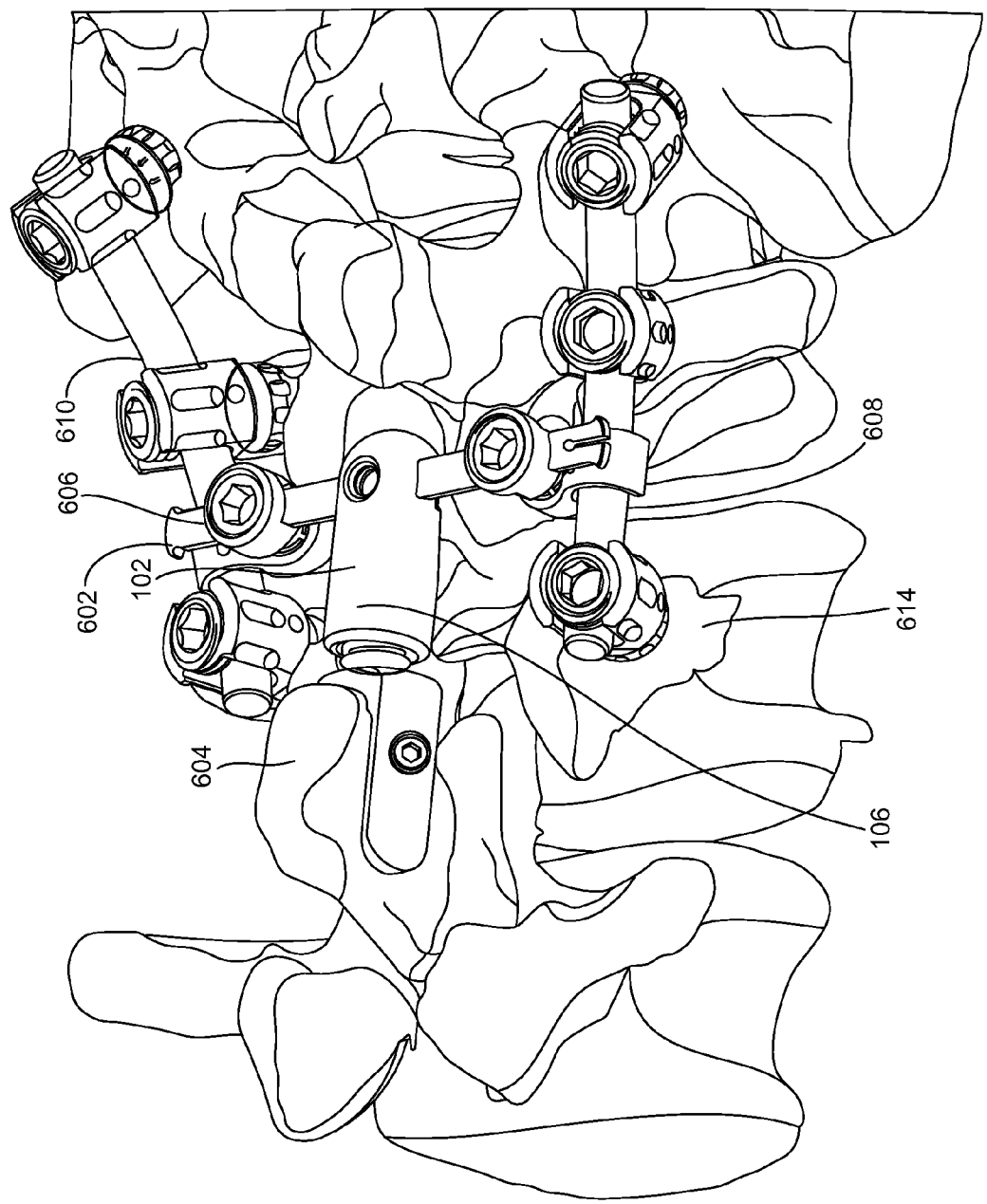

FIGS. 6A and 6B, with respect to FIGS. 1 through 5B, illustrate a front view and a side view, respectively, of the damper system 100 of FIG. 4 assembled into a vertebra according to an embodiment herein. The damper system 100 is connected to a spinal cross-connector assembly 602 (e.g., a device used to maintain and secure the posture of the vertebral column) and placed vertically in a vertebra. The spinal cross-connector assembly 602 may be capable of having an increased number of degrees of flexion and/or extension motion. The damper system 100 is placed between a fusion level and an adjacent posterior vertebral segment. The two arms 204, 206 along with the slot 208 of the U-shaped anchor 106 are attached with a lamina 604 (e.g., a flattened or arched part of the vertebra). The two screws 108, 110 passing through the two screw holes 208, 210, respectively, are fixed into the lamina 604. This prevents the decoupling of the U-shaped anchor 106 from the lamina 604.

A bar 606 of the cross-connector assembly 602 is linked with the cylindrical cap 102. The cross-opening 502 of the cylindrical cap 102 is adapted to facilitate the accommodation of the bar 606 of the cross connector assembly 602. The hole 114 of the cylindrical cap 102 may accommodate a screw or other blocker/fixation component (not shown) to set the bar 606 of the cross connector assembly 602 to the cylindrical cap 102 once inserted in the cross-opening 502. The cross-connector assembly 602 is connected to a pair of opposed polyaxial pedicle screw assemblies 608, 610 (e.g., devices used for connecting two adjacent vertebrae by spinal fusion).

The pair of polyaxial pedicle screw assemblies 608, 610 are anchored to pedicles 612, 614, respectively, (e.g., portions of the vertebra that connect the lamina to the body anteriorly and help to form the walls of the spinal canal). The pair of polyaxial pedicle screw assemblies 608, 610 may be utilized in surgeries with improved intra-operative flexibility to achieve lumbar interbody fusions and to cure degenerative disc diseases.

As the damper system 100 is attached between the cross-connector assembly 602 and the pair of polyaxial pedicle screw assemblies 608, 610 and fixed to the lamina 604, it protects and provides stability to the adjacent segments of the vertebral column. Moreover, while screws 108, 110 are illustrated in the drawings, those skilled in the art would understand that other types of fixation mechanisms such as fasteners, pins, nails could be used in lieu of screws. Additionally, the U-shaped anchor 106 may comprise other configurations (including non U-shaped configurations such as a rectangular bar) and may comprise corrugated teeth (not shown) that fix onto the lamina 604 rather than using screws 108, 110.

Figure 7:
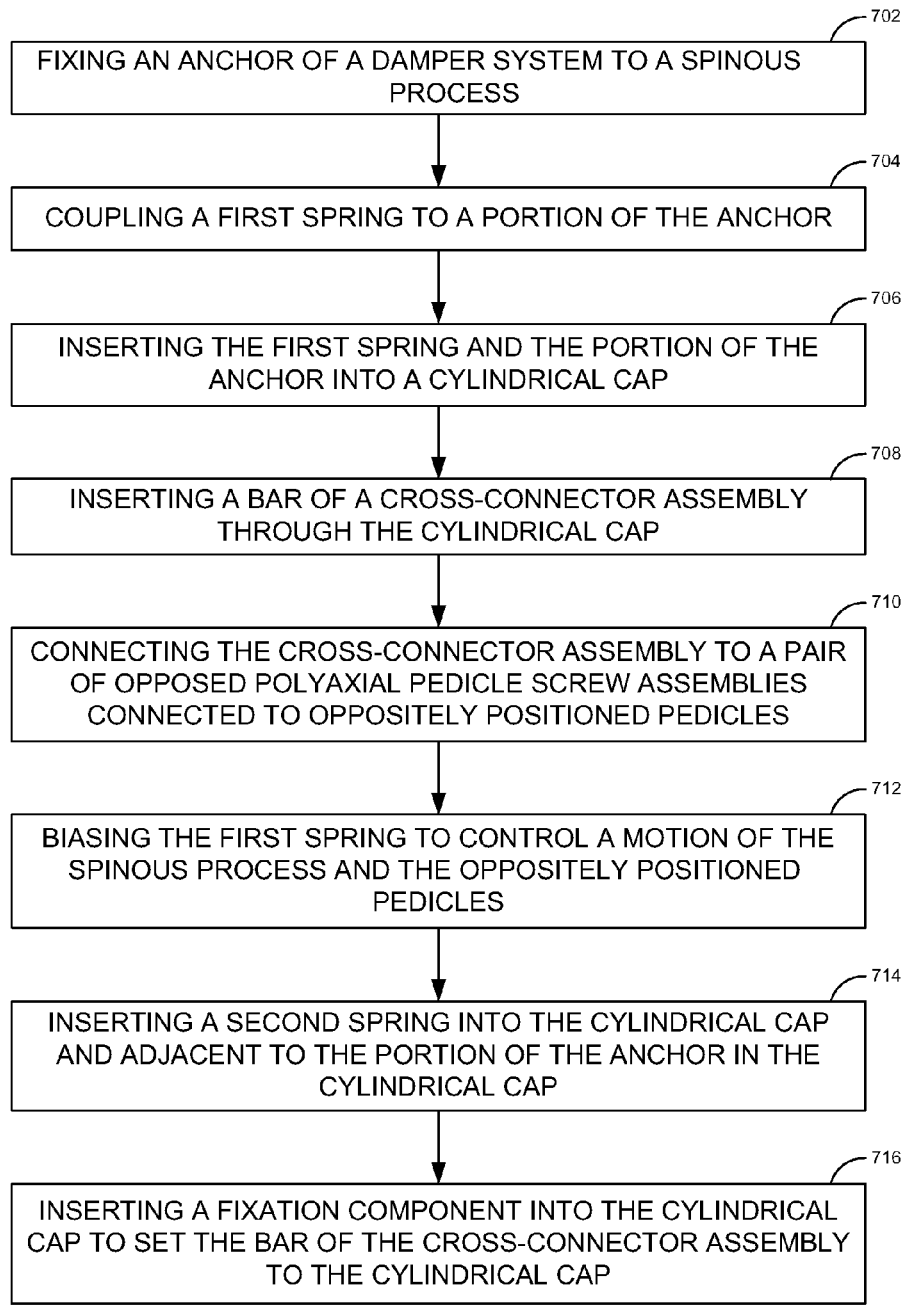
FIG. 7 illustrates a process flow illustrating a method of performing a surgical procedure according to an embodiment herein.

FIG. 7, with reference to FIGS. 1 through 6B, illustrates a process flow illustrating a method of controlling a degree of motion of a mobile vertebral segment according to an embodiment herein, wherein the method comprises fixing (702) an anchor 106 of a damper system 100 to a spinous process 604, coupling (704) a first spring 104 to a portion (e.g., the spring hitch 118) of the anchor 106, inserting (706) the first spring 104 and the portion 118 of the anchor 106 into a cylindrical cap 102, inserting (708) a bar 606 of a cross-connector assembly 602 through the cylindrical cap 102, connecting (710) the cross-connector assembly 602 to a pair of opposed polyaxial pedicle screw assemblies 608, 610 connected to oppositely positioned pedicles 612,614, biasing (712) the first spring 104 to control a motion of the spinous process 604 and oppositely positioned pedicles 612, 614, inserting (714) a second spring 504 into the cylindrical cap 102 and adjacent to the portion 118 of the anchor 106 in the cylindrical cap 102, and inserting (716) a fixation component (not shown) into the cylindrical cap 102 to set the bar 606 of the cross-connector assembly 602 to the cylindrical cap 102.

In step 702, the anchor 106 of the damper system 100 is fixed to a spinous process 604 (e.g., through the two arms 202, 204 of the anchor 106 as shown in FIGS. 6A and 6B). In step 704, the first spring 104 is coupled to the portion 118 of the anchor 106 (e.g., through the inner hollow area 116 of the spring 104 as shown in FIG. 3). In step 706, the first spring 104 and the portion 118 of the anchor 106 are inserted into the cylindrical cap 102 (e.g., through the inner cavity 112 of the cylindrical cap 102 as shown in FIG. 4). In step 708, the bar 606 of the cross-connector assembly 602 is inserted through the cylindrical cap 102 (e.g., through the cross opening 502). In step 710, the cross-connector assembly 602 is connected to the pair of opposed polyaxial pedicle screw assemblies 608, 610 connected to oppositely positioned pedicles 612,614 (e.g., as shown in FIGS. 6A and 6B). In step 712, the first spring 104 is biased to control a motion of the spinous process 604 and oppositely positioned pedicles 612,614. In step 714, the second spring 504 is inserted into the cylindrical cap 102 and adjacent to the portion 118 of the anchor 106 in the cylindrical cap 102. In step 716, the fixation component (not shown) is inserted into the cylindrical cap 102 to set the bar 606 of the cross-connector assembly 602 to the cylindrical cap 102.

The damper system 100 can be connected to any pedicle screw construct that has a cross-connector and can be added to any pedicle screw fusion. The damper system 100 works like a shock absorber and restrains the degree of flexion and/or extension of the mobile vertebral segment. Hence, the incidence and rate of progression of adjacent segment diseases is prophylactically reduced. The damper system 100 can also work when a laminectomy has been performed. The damper system 100 can be placed between the fusion level and the adjacent posterior element, thus providing additional stability to the adjacent motion segments and reducing the stresses that lead to early degeneration of the motion segment and requires no additional muscle dissection. Thus, the motion segment adjacent to a fusion remains both protected and functional.

The embodiments herein may work as follows. Once a patient undergoes a lumbar or thoracic fusion surgery for one or more levels, it is believed by most surgeons that the adjacent level disc is under increased stress due to the "unnatural" rigidity of the fused level(s). The embodiments herein provide a "load sharing" device 100 to share some of those increased forces on the healthy adjacent levels without compromising the pedicles of that adjacent level. Once a traditional fusion construct of four screws, two rods, and four blockers is implanted, the surgeon inserts a cross-connecting device 602 that either engages the two rods, or two opposing screws in the medial lateral direction to create a bridge between the two sides for the purpose of (a) assisting in the pull out resistance of the fusion construct, and (b) more importantly, providing a central point of fixation to engage the load sharing device 100. Once the cross-connector device 602 is inserted into the fusion hardware, the damper system assembly 100 is then fixated to the spinous process 604 of the adjacent level and the cross-connector 602, while the patient is positioned in the neutral zone of the patients range of motion. Then, the load sharing implant system 100 can provide a specific range of motion using its housed spring 104 or spring mechanism (such as polymers or a hydraulic system) to limit and dampen the motion as well as share the load of the healthy disc, therefore lengthening the life span of the adjacent disc. Preferably, the embodiments herein have a tensioned motion limited to +/−3 mm telescoping (axially) on the dampener mechanism 100, and through this same mechanism or the fixation point between the cross-connector bar 606 and the load sharing device 100, one may limit the flexion/extension and torsional movement to a few degrees in each direction.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An orthopedic damper system comprising:
    a U-shaped anchor adapted to connect to a spinous process, wherein said U-shaped anchor comprises a spring hitch;
    a spring coupled to said spring hitch, wherein said spring comprises an inner hollow area that accommodates said spring hitch; and
    a cap coupled to said spring, wherein said cap comprises:
        a non-bifurcated body;
        an opening connected to an inner cavity that accommodates said spring and said spring hitch, wherein said opening is positioned at a first end of said non-bifurcated body of said cap;
        a closed end positioned at a second end opposite to said first end of said non-bifurcated body, wherein a distance between said first end and said second end equals a total length of said cap;
        a partially threaded hole positioned proximate to said closed end; and
        a cross-opening positioned proximate to said closed end, wherein both said hole and said cross-opening are perpendicular to one another and are positioned at an end of said cap opposite to said opening of said cap.

2. The damper system of claim 1, wherein said U-shaped anchor further comprises:
    a plurality of arms each having a plurality of screw holes positioned opposite to said spring hitch; and
    a slot configured between said plurality of arms.

3. The damper system of claim 2, further comprising a plurality of retaining mechanisms that fixes into said spinous process, wherein said plurality of screw holes accommodate said plurality of retaining mechanisms, and said slot is adapted to accommodate said spinous process.

4. The damper system of claim 1, wherein said hole is bored completely through a first dimension of said cap and said hole further comprises threading etched completely along said first dimension of said hole.

5. The damper system of claim 4, wherein said cross-opening of said cap accommodates a bar of a cross-connector assembly.

6. The damper system of claim 4, wherein said hole of said cap accommodates a fixation component to set said bar of said cross-connector assembly to said cap.

7. The damper system of claim 5, wherein said cross-connector assembly connects with a pair of polyaxial pedicle screw assemblies.

8. An apparatus for stabilizing a vertebral segment, said apparatus comprising:
    an anchor adapted to connect to a spinous process, wherein said anchor comprises a clamping portion and a hitch connected to said clamping portion;
    fixation means that attaches said anchor to said spinous process;
    a first spring coupled to said anchor, wherein said first spring comprises an inner hollow area that accommodates said hitch of said anchor; and
    a cylindrical cap coupled to said first spring, wherein said cylindrical cap comprises:
        an opening leading to an inner cavity, wherein said inner cavity accommodates said first spring and said hitch of said anchor;
        a non-forked closed end positioned at an opposite end to said opening, wherein a distance between said opening and said closed end equals a total length of said cap;
        a cross-opening,
    wherein both said inner cavity and said cross-opening are perpendicular to one another, and
    wherein said cross-opening is positioned at an end of said cap opposite to said opening of said cap.

9. The apparatus of claim 8, further comprising a second spring positioned in said cylindrical cap and adjacent to said hitch.

10. The apparatus of claim 8, wherein said cross-opening of said cylindrical cap accommodates a bar of a cross-connector assembly.

11. The apparatus of claim 8, wherein said fixation means attaches said anchor to said spinous process, said fixation means comprises any of screws, fasteners, pins, nails, and corrugated teeth.

12. The apparatus of claim 10, wherein said cylindrical cap further comprises a hole that accommodates a fixation component to set said bar of said cross-connector assembly to said cylindrical cap.

13. The apparatus of claim 10, wherein said cross-connector assembly connects with a pair of oppositely positioned polyaxial pedicle screw assemblies.

14. A method of controlling a degree of motion of a mobile vertebral segment, said method comprising:

fixing an anchor of a damper system to a spinous process, wherein said damper system comprises said anchor, a spring comprising an inner hollow area that attaches to said anchor, and a non-forked cylindrical cap that accommodates said spring and a portion of said anchor, wherein said cylindrical cap comprises a threaded hole bored therethrough, and a cross-opening bored perpendicular to said threaded hole and intersecting said threaded hole;

coupling said spring to said portion of said anchor;

inserting said spring and said portion of said anchor into said cylindrical cap;

inserting a bar of a cross-connector assembly through said cross-opening of said cylindrical cap, wherein said bar of said cross-connector intersects said threaded hole;

connecting said cross-connector assembly to a pair of opposed polyaxial pedicle screw assemblies connected to oppositely positioned pedicles; and biasing said spring to control a motion of said spinous process and said oppositely positioned pedicles.

15. The method of claim 14, further comprising inserting a second spring into said cylindrical cap and adjacent to said portion of said anchor in said cylindrical cap.

16. The method of claim 14, further comprising inserting a fixation component into said cylindrical cap to set said bar of said cross-connector assembly to said cylindrical cap.

17. The method of claim 14, wherein said cross-connector assembly maintains and secures the posture of a vertebral column.

18. The method of claim 14, wherein said pair of opposed polyaxial pedicle screw assemblies connect two adjacent vertebrae by spinal fusion.

19. The method of claim 14, wherein said spring controls a degree of flexion of a vertebral segment.

20. The method of claim 14, wherein said anchor further comprises a slot that accommodates said spinous process.

* * * * *